United States Patent
Yamamoto (10) Patent No.: US 8,096,931 B2
(45) Date of Patent: Jan. 17, 2012

(54) CUTTING DEVICE AND MANUFACTURING METHOD FOR ABSORPTIVE ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 96 days.

(21) Appl. No.: 12/390,143

(22) Filed: Feb. 20, 2009

(65) Prior Publication Data

US 2010/0035740 A1 Feb. 11, 2010

(30) Foreign Application Priority Data

Aug. 7, 2008 (JP) ................................ P2008-204647

(51) Int. Cl.
*B31B 1/20* (2006.01)

(52) U.S. Cl. ........ 493/345; 493/343; 493/344; 493/370; 493/960; 83/109

(58) Field of Classification Search ................. 493/340, 493/343, 344, 345, 346, 354, 365, 369, 370, 493/960; 83/109
See application file for complete search history.

(56) References Cited

U.S. PATENT DOCUMENTS

| | | | | | |
|---|---|---|---|---|---|
| 3,607,578 | A | * | 9/1971 | Berg et al. | 156/552 |
| 3,666,611 | A | * | 5/1972 | Joa | 428/78 |
| 4,214,509 | A | * | 7/1980 | Van der Meulen | 493/191 |
| 4,284,454 | A | * | 8/1981 | Joa | 156/163 |
| 5,103,703 | A | * | 4/1992 | Littleton | 83/155 |
| 5,693,165 | A | * | 12/1997 | Schmitz | 156/164 |
| 6,820,671 | B2 | * | 11/2004 | Calvert | 156/543 |
| 6,915,621 | B2 | * | 7/2005 | Saraf et al. | 53/450 |
| 7,708,849 | B2 | * | 5/2010 | McCabe | 156/73.1 |
| 2002/0174930 | A1 | | 11/2002 | Umebayashi et al. | |
| 2004/0007328 | A1 | * | 1/2004 | Popp et al. | 156/494 |

FOREIGN PATENT DOCUMENTS

JP 2003-038566 A 2/2003

* cited by examiner

*Primary Examiner* — Christopher Harmon
(74) *Attorney, Agent, or Firm* — Lowe, Hauptman, Ham & Berner, LLP (57) ABSTRACT

A cutting device feeds a web between a die roll and an anvil roll, and cuts a continuous portion of the web. The cutting device includes a continuous portion transport unit configured to hold and transport the continuous portion of the web being continuous in a moving direction of the web, and a discontinuous portion transport unit configured to hold and transport a discontinuous portion of the web being discontinuous in the moving direction of the web. The die roll includes a first large diameter portion whose outer peripheral surface is provided with a cutting blade configured to cut the continuous portion of the web. The anvil roll includes a second large diameter portion disposed to face the first large diameter portion. By the discontinuous portion transport unit, the discontinuous portion passes through between the die roll and the anvil roll without contacting the first large diameter portion and the second large diameter portion.

14 Claims, 8 Drawing Sheets

CUTTING DEVICE AND MANUFACTURING METHOD FOR ABSORPTIVE ARTICLE

CROSS REFERENCE TO RELATED APPLICATIONS

This application is based upon and claims the benefit of priority from the prior Japanese Patent Application No. JP 2008-204647, filed on Aug. 7, 2008; the entire contents of which are incorporated herein by reference.

BACKGROUND OF THE INVENTION

1. Field of the Invention

The present invention relates to a cutting device and a method for manufacturing an absorptive article, in which a web is transported between a die roll and an anvil roll, and for cutting the web.

2. Description of the Related Art

Heretofore, the manufacturing method for an absorptive article, such as a disposable diaper, includes the following steps: 1) placing each of the members (e.g., a gather, a waterproof sheet, an absorber, and a top sheet) on a web; 2) cutting a leg opening region (e.g., a leg hole) corresponding to a leg opening portion; 3) folding the web in two; 4) and cutting the web to form an end-product absorptive article by using a cutting device (i.e., a product cut and shape). (See, for example, Japanese Patent Application Publication No. 2003-38566 (See pages. 2-4 and FIG. 1).)

The web being transported to go to the cutting step (the above-described 4); the product cut and shape), that is, the web being cut by the cutting device, includes a continuous portion and a discontinuous portion. The continuous portion is continuous in a moving direction (hereinafter, an MD direction) of the web, and corresponds to a waistband region of the absorptive article. On the other hand, the discontinuous portion corresponds to a crotch region and the leg opening region located between a pair of waistband regions, and has the leg opening region formed therein, thereby being discontinuous in the MD direction.

Here, the above-mentioned cutting device includes: a die roll whose outer peripheral surface is provided with a cutting blade configured to cut the continuous portion of the web; an anvil roll disposed to face the die roll; a continuous portion transport unit configured to transport the continuous portion to a region (hereinafter, a press-contact region) in which the die roll and the anvil roll contact and press each other; and an article transport unit configured to transport the absorptive article obtained through cutting the web by the cutting blade.

The continuous portion is transported from the continuous portion transport unit to between the die roll and the anvil roll (that is, to the press-contact region). Then, the continuous portion of the web is cut by the cutting blade. The absorptive article obtained through the cutting is transported from between the die roll and the anvil roll (that is, from the press-contact region) to the article transport unit.

Incidentally, it is important that the end-product absorptive article have a cut surface substantially parallel to a direction (hereinafter, a CD direction) crossing the MD direction, since the cut surface inclined relative to the CD direction can possibly cause manufacturing defects (e.g., bond failure), a poor appearance, or the like in the absorptive article.

In the above-mentioned conventional cutting device, however, the continuous portion of the web traveling from the continuous portion transport unit to the press-contact region is unheld/unnipped by the continuous portion transport unit. Similarly, the absorptive article traveling from the press-contact region to the article transport unit is unheld/unnipped by the article transport unit.

This can possibly lead to a displacement of the cut surface of the web when the cutting blade cuts the web. As a result, the continuous portion of the web may be cut in a displaced position. This causes the problem that the cut surface may be inclined relative to the CD direction, thereby causing the manufacturing defects or poor appearance in the absorptive-article obtained through the cutting.

The present invention has therefore been made in consideration of the above-described problems inherent in the related art. It is an object of the present invention to provide a cutting device and a manufacturing method for an absorptive article, which can suppress the manufacturing defects or poor appearance caused in the absorptive article.

SUMMARY OF THE INVENTION

An aspect of the present invention is summarized as a cutting device for transporting a web between a die roll and an anvil roll and for cutting the web. The cutting device includes a first belt conveyor configured to hold and transport a continuous portion of the web of the web being continuous in a moving direction of the web, and a second belt conveyor configured to hold and transport a discontinuous portion of the web being discontinuous in the moving direction of the web. The die roll includes a first large diameter portion whose outer peripheral surface is provided with a cutting blade configured to cut a continuous portion of the web. The anvil roll includes a second large diameter portion disposed to face the first large diameter portion. The first belt conveyor is configured to feed the continuous portion to a region in which the first large diameter portion and the second large diameter portion contact and press each other. By the second belt conveyor, the discontinuous portion passes through between the die roll and the anvil roll without contacting the first large diameter portion and the second large diameter portion.

The present invention can provide the cutting device and the manufacturing method for the absorptive article, which can suppress the manufacturing defects or a poor appearance caused in the absorptive article.

DETAILED DESCRIPTION OF THE PREFERRED EMBODIMENTS

Description will be given below with reference to the drawings with regard to embodiments of the present invention. Specifically, description will be given with regard to (1) a manufacturing method for an absorptive article, (2) the configuration of a cutting device, (3) the configuration of a continuous portion transport unit, (4) the configuration of a discontinuous portion transport unit, (5) the configuration of an article transport unit, (6) operations and effects, (7) modified embodiments, and (8) other embodiments.

Note that, throughout the drawings, the same or similar parts are designated by the same or similar reference numerals. It should be noted that the drawings are in schematic form and dimensional ratios and others therein are different from actual ones.

It is to be therefore understood that specific dimensions and others should be determined based on the following description. Of course, it will be also understood that differences may be existed in the relations or ratios between dimensions in the drawings as cross-referred.

(1) A Manufacturing Method for an Absorptive Article

Figure 1:
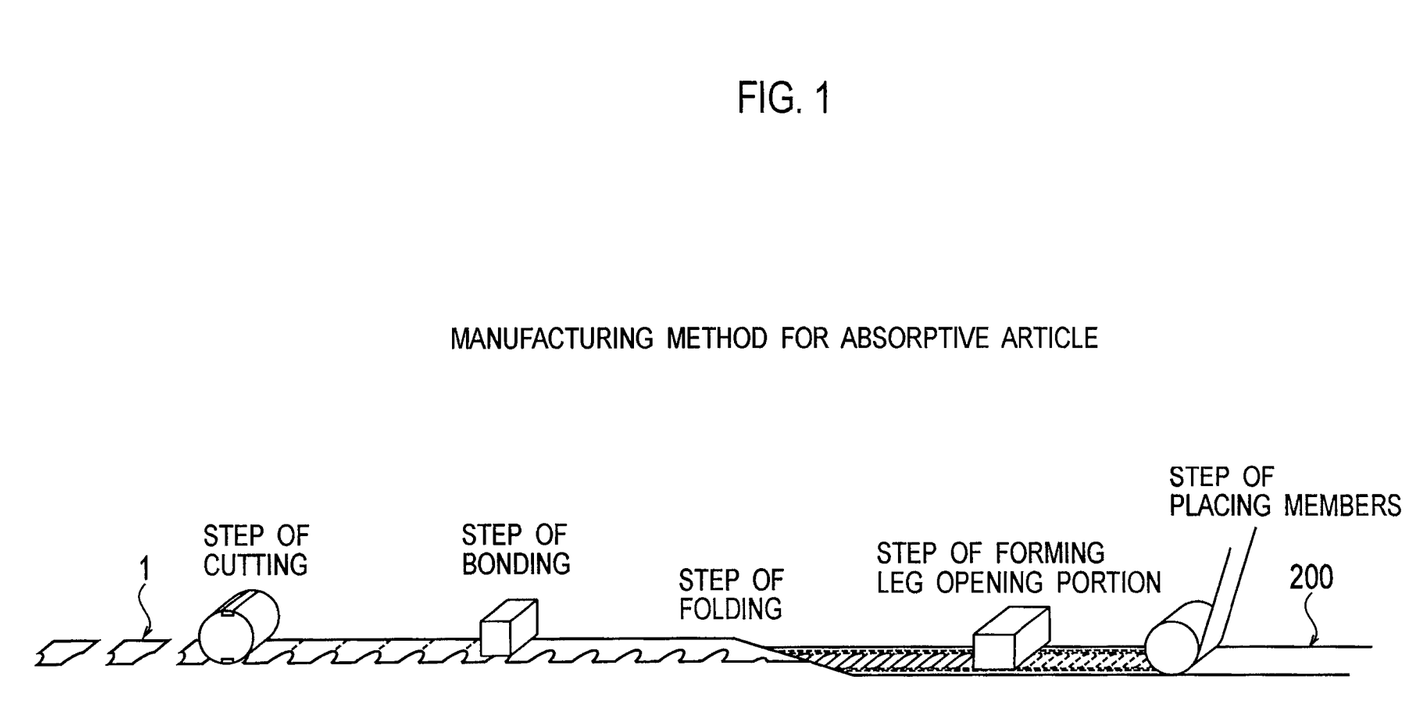
FIG. 1 is a schematic view illustrating a manufacturing method for an absorptive article 1 according to an embodiment of the present invention.
Figure 2A:
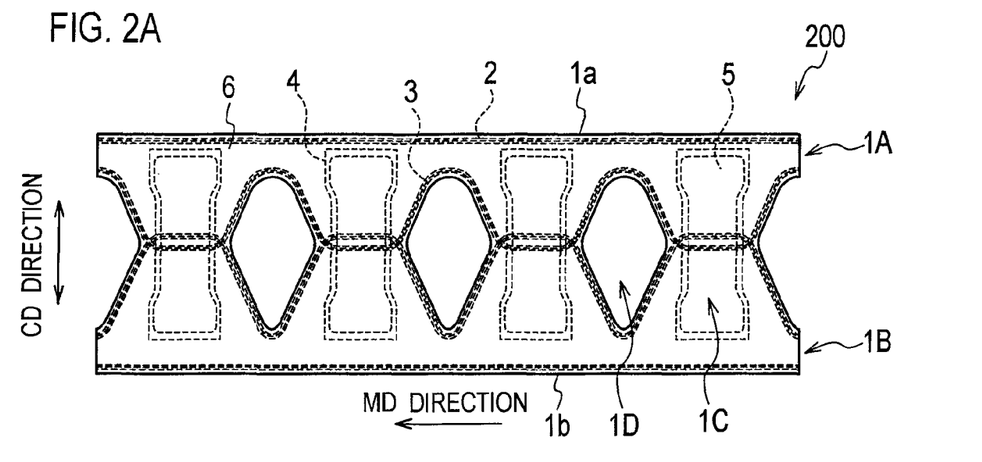
FIGS. 2A to 2C are views showing a web 200 (or the absorptive article 1) according to the embodiment of the present invention.
Figure 2B:
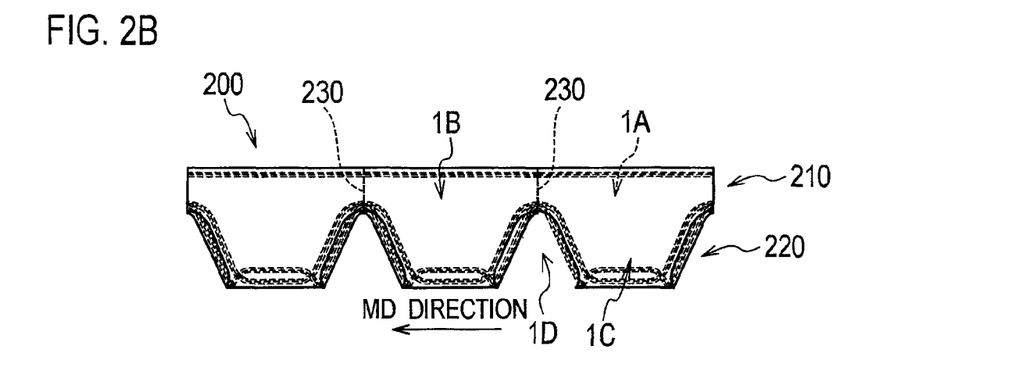
Figure 2C:
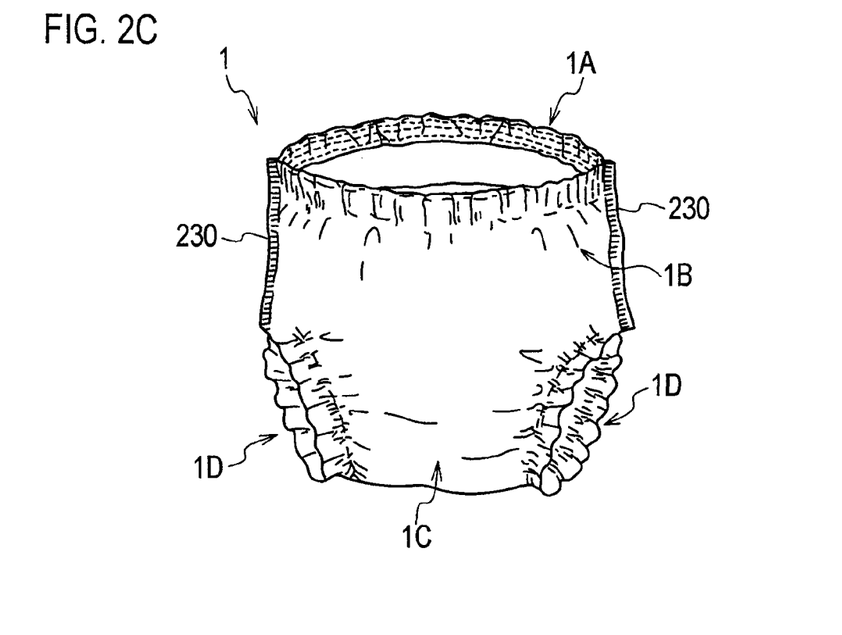

Firstly, description will be given with reference to FIG. 1 and FIGS. 2A to 2C with regard to a manufacturing method for an absorptive article 1 according to an embodiment of the present invention. FIG. 1 is a schematic view illustrating the manufacturing method for the absorptive article 1 according to the embodiment of the present invention. FIGS. 2A to 2C are views showing a web 200 (to be the absorptive articles 1) according to the embodiment of the present invention. Incidentally, the absorptive article 1 according to the embodiment of the present invention is a disposable diaper having a waistband member.

As shown in FIG. 1, the manufacturing method for the absorptive article 1 includes at least a step of placing members, a step of forming a leg opening portion, a step of folding the web, a step of bonding, and a step of cutting.

(1-1) The Step of Placing the Members

In the step of placing the members, each of the members is placed on the web 200 (e.g., a continuum of an outer sheet). The members include gathers (e.g., a fit gather 2 and a leg gather 3), a waterproof sheet 4, an absorber 5, and a top sheet 6, as shown for example in FIG. 2A.

Here, as shown in FIGS. 2A and 2B, the web 200 includes waistband regions 1A and 1B corresponding to the waistband member (or a waistband portion) of the absorptive article 1, a crotch region 1C located between the waistband regions 1A and 1B, and a leg opening region 1D located on both sides of each crotch region 1C.

The waistband regions 1A and 1B have the property of stretching in the moving direction (or the MD direction) of the web 200. Here, "the waistband regions 1A and 1B have the property of stretching" indicates, for example, that the provision of the fit gather 2 renders these regions stretchable, that the web 200 in itself is made of a sheet having stretching properties, or the like.

The crotch region 1C has the property of stretching in a direction (or the CD direction) crossing to the MD direction. Here, "the crotch region 1C has the property of stretching" indicates, for example, that the provision of the leg gather 3 renders this region stretchable, that the web 200 in itself is made of a sheet having stretching properties, or the like.

(1-2) The Step of Forming the Leg Opening Portion

The step of forming the leg opening portion includes: forming the leg opening regions 1D (e.g., leg holes) on the web 200.

(1-3) The Step of Folding the Web

The step of folding the web includes folding the web 200 in two, at the center of the web 200 in the CD direction. The web 200 is folded at the crotch regions 1C so that an end 1a of the waistband region 1A is aligned with an end 1b of the waistband region 1B (see FIG. 2B).

Here, the web 200 folded in two includes a continuous portion 210 and a discontinuous portion 220. The continuous portion 210 is continuous in the MD direction and includes the waistband regions 1A and 1B. On the other hand, the discontinuous portion 220 is discontinuous in the MD direction and includes the crotch regions 1C and the leg opening regions 1D.

(1-4) The Step of Bonding

In the step of bonding, a cut surface 230 of the continuous portion 210, that is, a boundary region of each absorptive article 1, is bonded by using an ultrasonic bonding method, a heat embossing method, or the like. Note that, the bonding step is performed between the step of folding the web and the step of cutting.

(1-5) The Step of Cutting

In the step of cutting, the cut surface 230 (or the boundary region) of the continuous portion 210 is cut to form the absorptive article 1 (see FIG. 2C), by using a cutting device 100 to be described later.

(2) The Configuration of the Cutting Device

Figure 3:
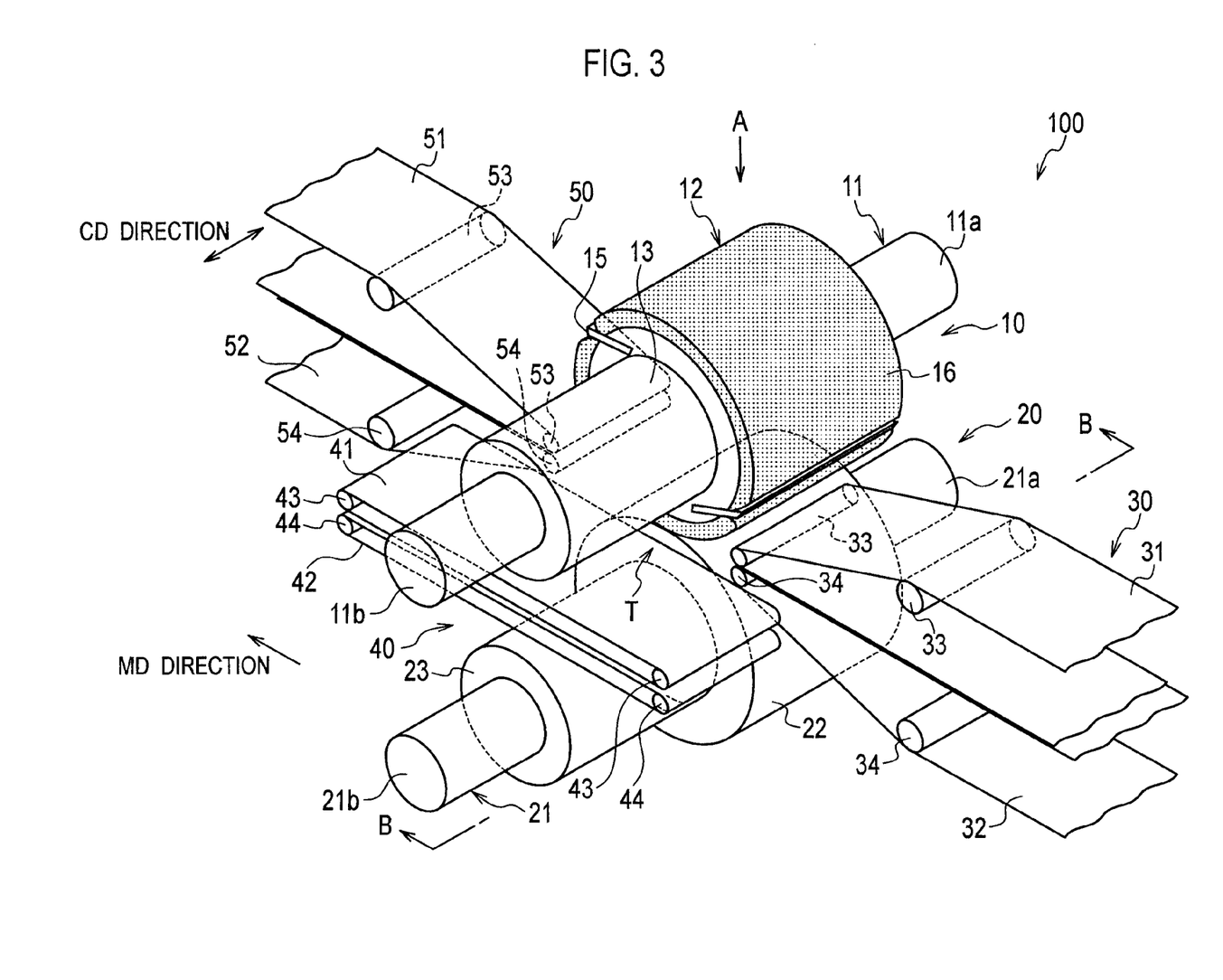
FIG. 3 is a partial perspective view showing a cutting device 100 according to the embodiment of the present invention.
Figure 4:
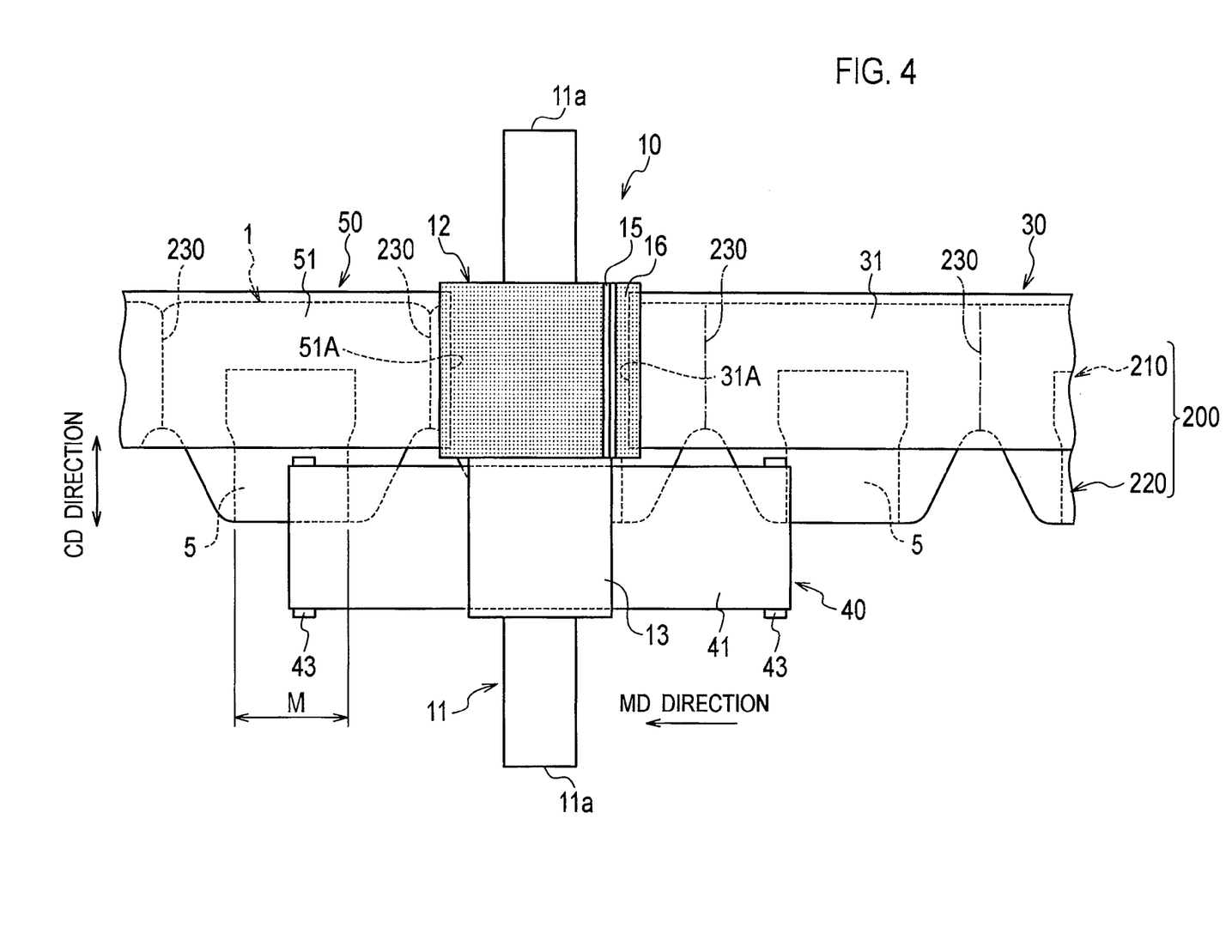
FIG. 4 is a top view showing the cutting device 100 according to the embodiment of the present invention (as viewed in the direction of the arrow A of FIG. 3).
Figure 5:
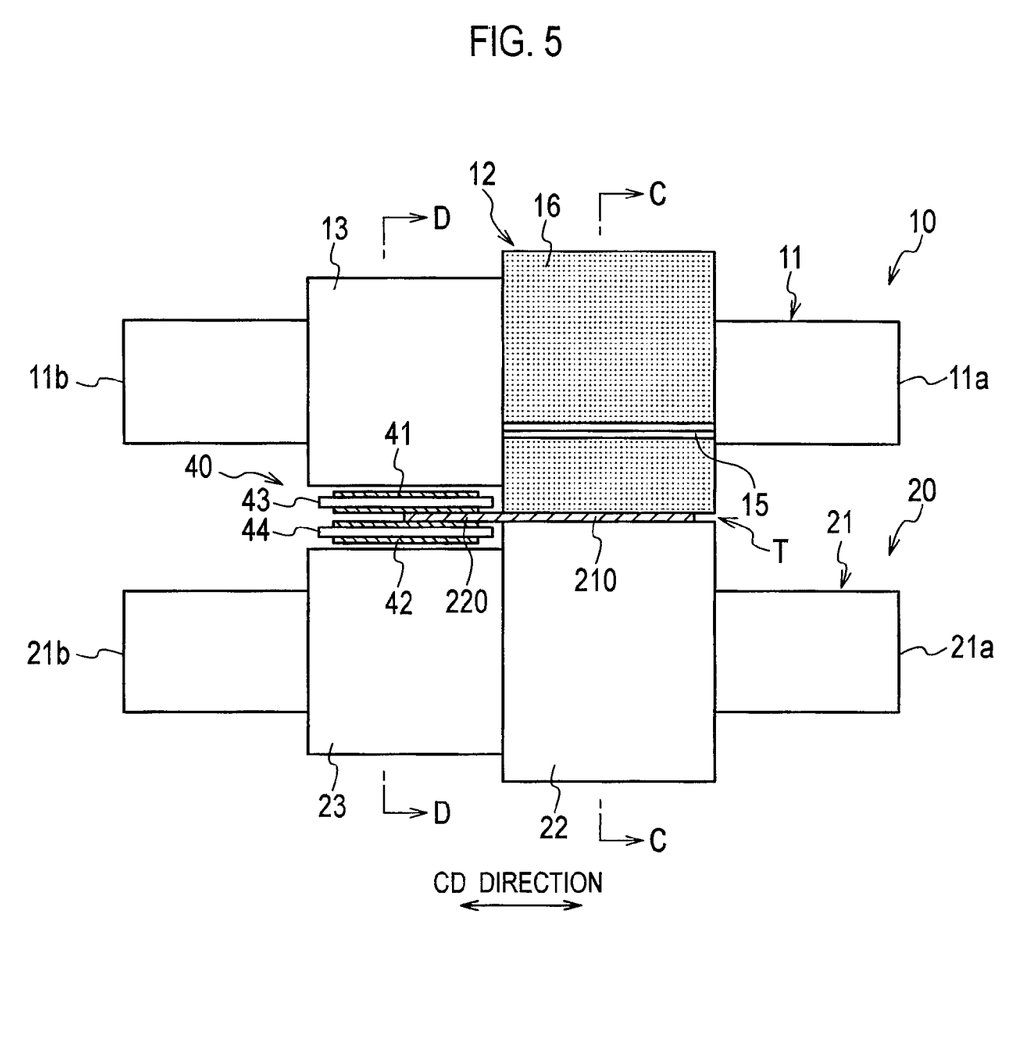
FIG. 5 is a partial sectional view (taken along the line B-B of FIG. 3) showing the cutting device 100 according to the embodiment of the present invention.

Description will now be given with reference to FIGS. 3 to 5 with regard to the cutting device 100 according to the embodiment of the present invention. FIG. 3 is a partial perspective view showing the cutting device 100 according to the embodiment of the present invention. FIG. 4 is a top view showing the cutting device 100 according to the embodiment of the present invention (as viewed in the direction of the arrow A of FIG. 3). FIG. 5 is a partial sectional view (taken along the line B-B of FIG. 3) showing the cutting device 100 according to the embodiment of the present invention.

As shown in FIGS. 3 to 5, the cutting device 100 cuts the continuous portion 210 so that the cut surface 230 (see FIG. 4) of the continuous portion 210 may be substantially parallel to the CD direction. Specifically, the cutting device 100 includes a die roll 10, an anvil roll 20, a continuous portion transport unit 30, a discontinuous portion transport unit 40, and an article transport unit 50.

The die roll 10 includes a first shaft member 11 rotated by a driving unit (not shown), a first large diameter portion 12 provided integrally with the first shaft member 11, and a first small diameter portion 13 integral with the first shaft member 11 and having a smaller diameter than the first large diameter portion 12.

Both ends 11a and 11b of the first shaft member 11 are connected to a frame (not shown). The first large diameter portion 12 and the first small diameter portion 13 are disposed coaxially with the first shaft member 11.

The outer peripheral surface of the first large diameter portion 12 is provided with a cutting blade 15 configured to cut the continuous portion 210. The outer peripheral surface of the first large diameter portion 12 is provided with a nipping member 16 configured to hold and nip the continuous portion 210 between the die roll 10 and the anvil roll 20 (or a second large diameter portion 22 to be described later). Note that, the nipping member 16 is disposed on the outer peripheral surface of the first large diameter portion 12, except for the outer peripheral surface provided with the cutting blade 15.

Here, the nipping member 16 may be made of, for example, a sponge, a metal spring, a needle, or the like. In other words, the nipping member 16 may be made of any material, provided that the nipping member 16 can hold and nip the continuous portion 210 between the die roll 10 and the anvil roll 20.

The anvil roll 20 includes a second shaft member 21, a second large diameter portion 22, and a second small diameter portion 23. The second shaft member 21 is rotated by a driving unit (not shown). The second large diameter portion 22 is provided integrally with the second shaft member 21. The second small diameter portion 23 is provided integrally with the second shaft member 21 and having a smaller diameter than the second large diameter portion 22.

Both ends 21a and 21b of the second shaft member 21 are connected to a frame (not shown). The second large diameter portion 22 and the second small diameter portion 23 are disposed coaxially with the second shaft member 21. The second large diameter portion 22 and the second small diameter portion 23 are disposed to face the first large diameter portion 12 and the first small diameter portion 13, respectively.

The continuous portion transport unit 30 is configured of a first belt conveyor. The first belt conveyor transports the continuous portion 210 while holding the continuous portion 210. The configuration of the continuous portion transport unit 30 will be described later (see FIGS. 3 to 6).

The discontinuous portion transport unit 40 is configured of a second belt conveyor. The second belt conveyor transports the discontinuous portion 220 while holding the discontinuous portion 220, when the continuous portion 210 is cut by the cutting blade 15 of the die roll 10 (hereinafter, at the time of web cutting). The configuration of the discontinuous portion transport unit 40 will be described later (see FIGS. 3 to 5 and FIG. 7).

The article transport unit 50 is configured of a third belt conveyor. The third belt conveyor transports the absorptive article 1 obtained through cutting the continuous portion 210 by the cutting blade 15 of the die roll 10, while holding the absorptive article 1. The configuration of the article transport unit 50 will be described later (see FIGS. 3 to 6).

(3) The Configuration of the Continuous Portion Transport Unit

Figure 6:
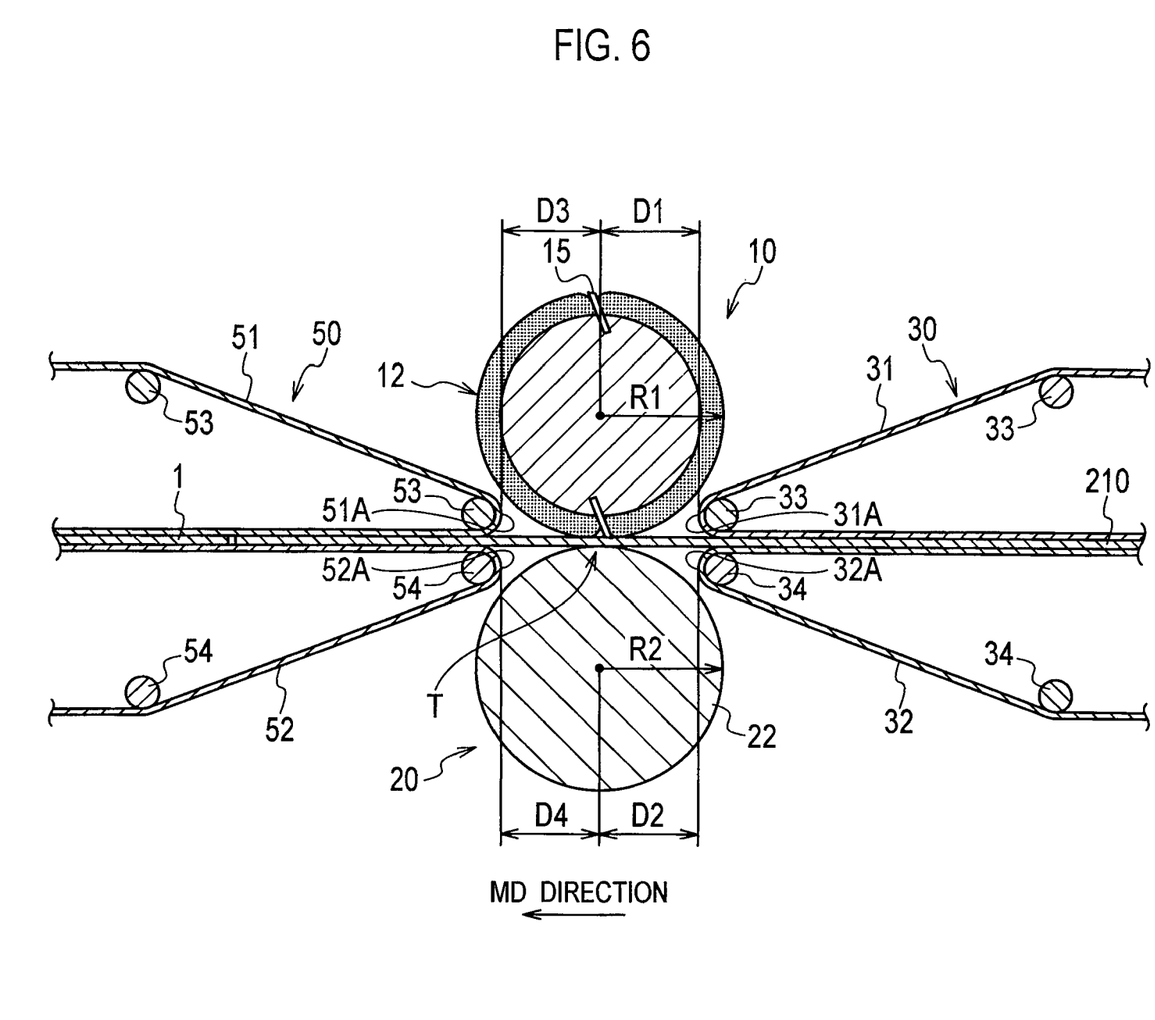
FIG. 6 is a sectional view (taken along the line C-C of FIG. 5) showing the cutting device 100 according to the embodiment of the present invention.

Description will now be given with reference to FIGS. 3 to 6 with regard to the configuration of the continuous portion transport unit 30 according to the embodiment of the present invention. Note that, FIG. 6 is a sectional view (taken along the line C-C of FIG. 5) showing the cutting device 100 according to the embodiment of the present invention.

As shown in FIGS. 3 to 6, the continuous portion transport unit 30 is configured to feed the continuous portion 210 to a region (hereinafter, a press-contact region T) in which the die roll 10 (or the first large diameter portion 12) and the anvil roll 20 (or the second large diameter portion 22) contact and press each other.

Specifically, the continuous portion transport unit 30 includes a first upper belt 31 located above the continuous portion 210, and a first lower belt 32 located under the continuous portion 210.

The first upper belt 31 is wound around a plurality of rollers 33. A distance (D1) from an end 31A of the first upper belt 31 at the die roll 10 side to the press-contact region T is shorter than a radius (R1) of the die roll 10. Incidentally, the radius (R1) of the die roll 10 includes the above-mentioned nipping member 16. In other words, the radius (R1) of the die roll 10 indicates a distance from the center of the die roll 10 to the outer peripheral surface of the nipping member 16. Here, it is preferable that the distance (D1) be shorter than a length (M) of the absorber 5 (see FIG. 4) in the MD direction.

The first lower belt 32 is wound around a plurality of rollers 34. A distance (D2) from an end 32A of the first lower belt 32 at the die roll 10 side to the press-contact region T is shorter than a radius (R2) of the anvil roll 20. Here, it is preferable that the distance (D2) be shorter than the length (M) of the absorber 5 (see FIG. 4) in the MD direction.

(4) The Configuration of the Discontinuous Portion Transport Unit

Figure 7:
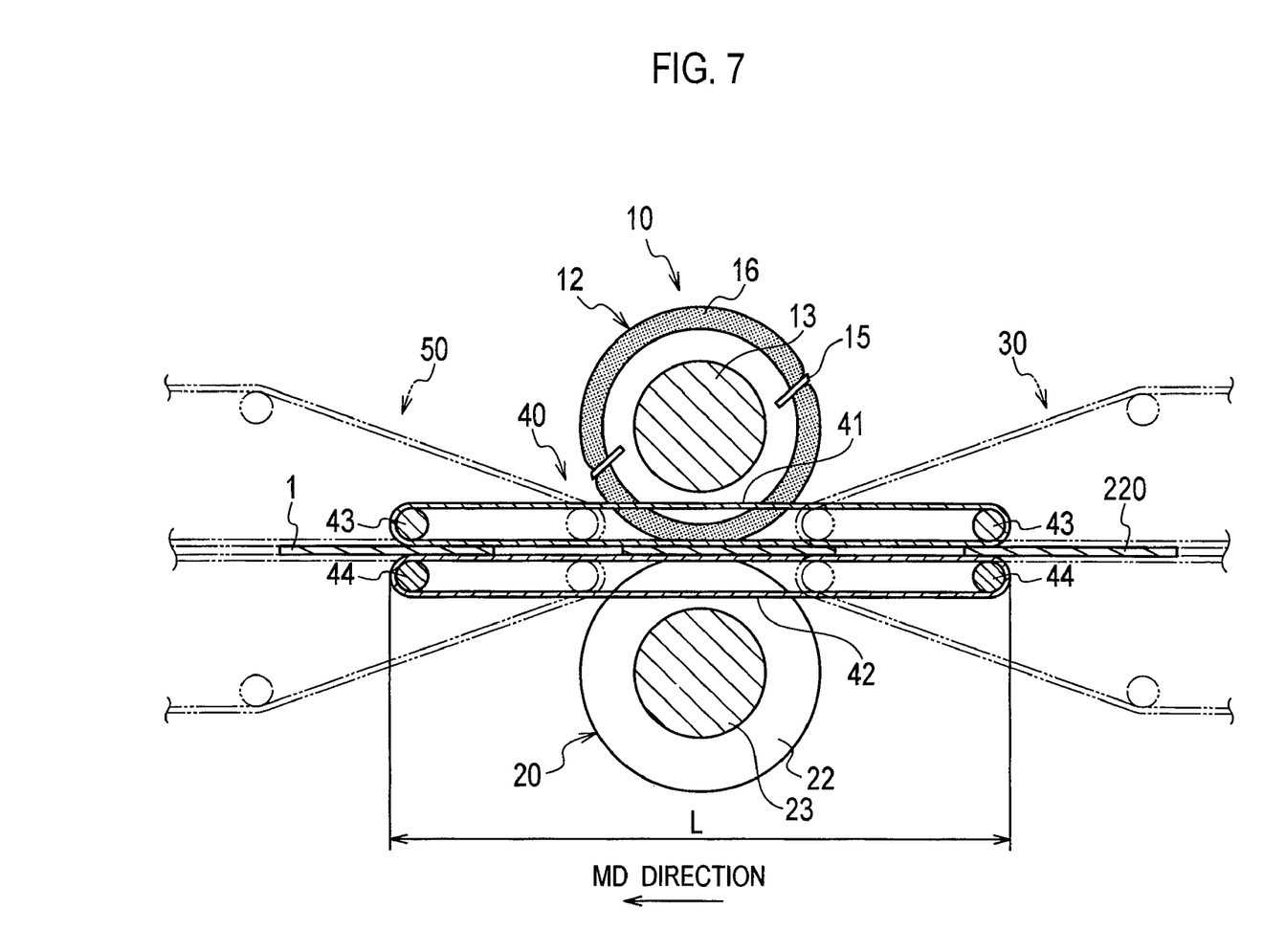
FIG. 7 is a sectional view (taken along the line D-D of FIG. 5) showing the cutting device 100 according to the embodiment of the present invention.

Description will now be given with reference to FIGS. 3 to 5 and FIG. 7 with regard to the configuration of the discontinuous portion transport unit 40 according to the embodiment of the present invention. Incidentally, FIG. 7 is a sectional view (taken along the line D-D of FIG. 5) showing the cutting device 100 according to the embodiment of the present invention.

As shown in FIGS. 3 to 5 and FIG. 7, by the discontinuous portion transport unit 40, the discontinuous portion 220 passes through between the die roll 10 and the anvil roll 20 without contacting the first large diameter portion 12 and the second large diameter portion 22.

Specifically, the discontinuous portion transport unit 40 includes a second upper belt 41 located above the discontinuous portion 220, and a second lower belt 42 located under the discontinuous portion 220.

The second upper belt 41 is wound around a plurality of rollers 43. Similarly, the second lower belt 42 is wound around a plurality of rollers 44.

The maximum length (hereinafter, a belt length L) of the second upper belt 41 and the second lower belt 42 can be arbitrary set, provided that, the discontinuous portion 220 can be held and nipped between the second upper belt 41 and the second lower belt 42 at the time of web cutting. For example, the belt length L is set so that the discontinuous portion 220 corresponding to at least one absorptive article 1 (or one end-product crotch region 1C) can be held and nipped between the second upper belt 41 and the second lower belt 42.

(5) The Configuration of the Article Transport Unit

Description will now be given with reference to FIGS. 3 to 6 with regard to the configuration of the article transport unit 50 according to the embodiment of the present invention.

As shown in FIGS. 3 to 6, the article transport unit 50 is configured to transport the web 200 after traveling through the press-contact region T (that is, the absorptive article 1 obtained through cutting the continuous portion 210 by the cutting blade 15), to the following step (e.g., a step of inspection).

Specifically, the article transport unit 50 includes a third upper belt 51t located above the absorptive article 1, and a third lower belt 52 located under the absorptive article 1.

The third upper belt 51 is wound around a plurality of rollers 53. A distance (D3) from an end 51A of the third upper belt 51 at the die roll 10 side to the press-contact region T is shorter than the radius (R1) of the die roll 10. In particular, it is preferable that the distance (D3) be shorter than the length (M) of the absorber 5 (see FIG. 4) in the MD direction.

The third lower belt 52 is wound around a plurality of rollers 54. A distance (D4) from an end 52A of the third lower belt 52 at the die roll 10 side to the press-contact region T is shorter than the radius (R2) of the anvil roll 20. In particular, it is preferable that the distance (D4) be shorter than the length (M) of the absorber 5 (see FIG. 4) in the MD direction.

(6) Operations and Effects

Generally, in the step of cutting the web, when the cut surface 230 (or the boundary region) of the continuous portion 210 is cut, the continuous portion 210 traveling from the continuous portion transport unit 30 to the press-contact region T becomes unheld/unnipped, since the waistband regions 1A and 1B have the property of stretching in the MD direction. Thus, the waistband regions 1A and 1B shrink, and delays the timing of the cutting of the continuous portion 210 by the cutting device 100 (or the cutting blade 15). In particular, the web 200 has difficulty in entering the press-contact region T, since the web 200 is made of a soft material. Additionally, the crotch region 1C has the property of stretching in the CD direction, thereby the crotch region 1C can possibly delay the timing of the cutting, as in the case of the waistband regions 1A and 1B. This makes the web more difficult to enter the press-contact region T.

Accordingly, in the above-described embodiment, by the discontinuous portion transport unit 40, the discontinuous portion 220 passes through between the die roll 10 (or the first large diameter portion 12) and the anvil roll 20 (or the second large diameter portion 22) without contacting the die roll 10 (or the first large diameter portion 12) and the anvil roll 20 (or the second large diameter portion 22). Thereby, the discontinuous portion 220 can be transported from the continuous portion transport unit 30 to the discontinuous portion transport unit 40, before the continuous portion 210 is transported from the continuous portion transport unit 30 to the press-contact region T. Further, the cut surface 230 (or the boundary region) of the continuous portion 210 is cut by the cutting device 100 (or the cutting blade 15), while the discontinuous portion 220 is being transported by the discontinuous portion transport unit 40. This makes it possible to transport the continuous portion 210 stably to the press-contact region T and to prevent the displacement of the continuous portion 210, at the time of web cutting. Therefore, this enables eliminating the step of cutting the continuous portion 210 in a displaced position, or equivalently, preventing the cut surface 230 from being inclined relative to the CD direction. As a result, manufacturing defects or poor appearance can be prevented in the absorptive article 1 obtained through cutting the continuous portion 210.

According to the above-described embodiment, the distance (D1) from the ends (namely, the ends 31A and 32A) of the continuous portion transport unit 30 at the die roll 10 side to the press-contact region T is shorter than the radius (R1) of the die roll 10. Thereby, the continuous portion transport unit 30 can hold and nip the continuous portion 210 as long as possible before the continuous portion 210 reaches the vicinity of the press-contact region T Therefore, the displacement of the continuous portion 210 can be further prevented.

According to the above-described embodiment, the cutting device 100 further includes the article transport unit 50, in addition to the continuous portion transport unit 30 and the discontinuous portion transport unit 40. Thereby, the absorptive article 1 obtained through the cutting is transported from the discontinuous portion transport unit 40 to the article transport unit 50. Thus, the absorptive article 1 does not become unheld/unnipped, thereby making it possible to stably transport the absorptive article 1, in addition to the continuous portion 210.

According to the above-described embodiment, the outer peripheral surface of the first large diameter portion 12 is provided with the nipping member 16 configured to hold and nip the continuous portion 210 between the first large diameter portion 12 and the second large diameter portion 22. Thereby, the continuous portion 210 can be held and nipped in the press-contact region T, even at any time other than the time of web cutting. Therefore, displacement of the continuous portion 210 can be further prevented.

(7) Modified Embodiments

The die roll 10 and the anvil roll 20 described in the above embodiment may be modified as below. Note that, the parts identical or similar to those of the cutting device according to the above-mentioned embodiment are designated by the identical or similar reference numerals, and differences will be mainly described.

Figure 8:
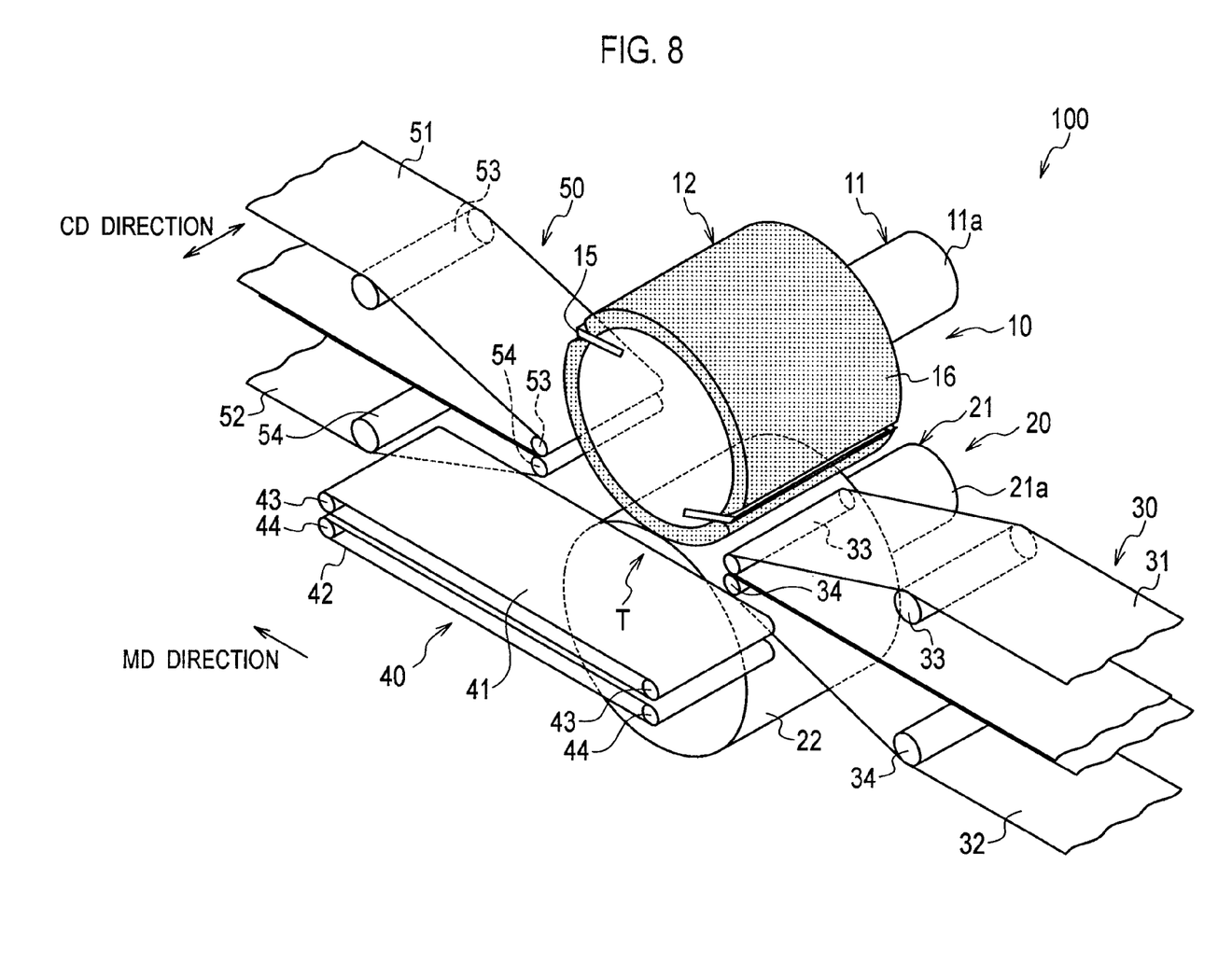
FIG. 8 is a partial perspective view showing the cutting device 100 according to a modified embodiment.

FIG. 8 is a partial perspective view showing the cutting device 100 according to a modified embodiment. As shown in FIG. 8, the die roll 10 includes the first shaft member 11 and the first large diameter portion 12. In other words, the die roll 10 does not include the first small diameter portion whose diameter is smaller than the diameter of the first large diameter portion 12. Incidentally, one end 11a of the first shaft member 11 is linked to the frame (not shown).

The anvil roll 20 includes the second shaft member 21 and the second large diameter portion 22. In other words, the anvil roll 20 does not include the second small diameter portion whose diameter is smaller than the diameter of the second large diameter portion 22. Incidentally, the one end 21a of the second shaft member 21 is connected to the frame (not shown).

In the cutting device 100 according to the modified embodiment, the die roll 10 does not include the first small diameter portion, and the anvil roll 20 does not include the second small diameter portion. This achieves simplification of the configuration of the cutting device 100 and thus enables reducing the manufacturing cost of the cutting device 100.

It should be noted that, as a matter of course, any one of the die roll 10 and the anvil roll 20 may have the second small diameter portion.

(8) Other Embodiments

Although the disclosure of the present invention has been given by way of the embodiments of the present invention as mentioned above, it is to be understood that the description and drawings that form part of this disclosure are not intended to limit the scope of the invention.

Specifically, the description has been provided for the discontinuous portion transport unit 40 including a pair of belts (namely, the second upper belt 41 and the second lower belt 42), but it is not limited to the foregoing. For example, one belt capable of sucking the discontinuous portion 220 may be used as the discontinuous portion transport unit 40.

Similarly, the continuous portion transport unit 30 or the article transport unit 50 is not necessarily formed of a pair of belts, but may be formed of one belt capable of sucking the continuous portion 210 or the absorptive article 1. Note that, the cutting device 100 does not necessarily include the article transport unit 50.

Also, the continuous portion transport unit 30 has been described as feeding the continuous portion 210 to the press-contact region T by holding and nipping the continuous portion 210 between the first upper belt 31 and the first lower belt 32; however, it is not limited to this configuration. For example, the continuous portion transport unit 30 may be configured to feed the continuous portion 210 to the press-contact region T by holding and nipping the continuous portion 210 between the outer peripheral surface of the anvil roll 20 and one belt disposed opposite the outer peripheral surface.

Similarly, the discontinuous portion transport unit 40 has been described as transporting the discontinuous portion 220 from the press-contact region T, by holding and nipping the discontinuous portion 220 between the second upper belt 41 and the second lower belt 42. However, it is not limited to this configuration. For example, the discontinuous portion transport unit 40 may be configured to transport the discontinuous portion 220 from the press-contact region T by holding and nipping the discontinuous portion 220 between the outer peripheral surface of the anvil roll 20 and one belt disposed opposite the outer peripheral surface.

It should be noted that, as a matter of course, the article transport unit 50 may be configured to hold and nip the continuous portion 210 between the outer peripheral surface of the anvil roll 20 and one belt disposed opposite the outer peripheral surface, as in the case of the continuous portion transport unit 30 or the discontinuous portion transport unit 40.

Further, the first large diameter portion 12 and the first small diameter portion 13 of the die roll 10 have been described as being provided integrally with the first shaft member 11; however, it is not limited to this configuration. The first large diameter portion 12 and the first small diameter portion 13 may be provided separately from the first shaft member 11. Similarly, the second large diameter portion 22 and the second small diameter portion 23 of the anvil roll 20 have been described as being provided integrally with the second shaft member 21; however, it is not limited to this configuration. The second large diameter portion 22 and the second small diameter portion 23 may be provided separately from the second shaft member 21.

From this disclosure, various alternative embodiments, examples and practical technologies will be obvious to those skilled in the art. It is to be therefore understood that the technological scope of the invention is determined only by claimed elements according to the scope of claims reasonably understood from the foregoing description.

What is claimed is:

1. A cutting device for cutting a web used in a process of manufacturing an absorptive article,
    wherein the web includes,
        a continuous portion which is continuous in a machine direction transverse to a cross direction, and
        a discontinuous portion which is discontinuous in the machine direction, wherein the continuous portion and the discontinuous portion are disposed side by side in the cross direction,
    said cutting device comprising:
    a die roll including a first large diameter portion whose outer peripheral surface is provided with a cutting blade configured to cut the continuous portion of the web;
    an anvil roll including a second large diameter portion disposed to face the first large diameter portion and defining with the first large diameter portion a region in which the first large diameter portion and the second large diameter portion contact and press each other and in which the continuous portion of the web is to be cut;
    a first belt conveyor configured to hold and transport the continuous portion of the web downstream in the machine direction toward said region; and
    a second belt conveyor configured to hold and transport the discontinuous portion of the web downstream in the machine direction, alongside said region, and without the discontinuous portion contacting the first large diameter portion and the second large diameter portion,
    wherein
    any one of the die roll and the anvil roll further includes a small diameter portion coaxial with and smaller in diameter than a corresponding one of the first large diameter portion and the second large diameter portion, and
    said second belt conveyor, together with the discontinuous portion to be held and transported by said second belt conveyor, passes through between the die roll and the anvil roll, at a side where the small diameter portion is provided.

2. The cutting device according to claim 1, wherein
    the first belt conveyor includes a first upper belt and a first lower belt, which are configured to hold and nip the continuous portion of the web between the first upper belt and the first lower belt, and
    the second belt conveyor includes a second upper belt and a second lower belt, which are configured to hold and nip the discontinuous portion of the web between the second upper belt and the second lower belt.

3. The cutting device according to claim 1, wherein
    a distance from an end of the first belt conveyor adjacent the die roll to said region in which the die roll and the anvil roll contact and press each other is shorter than a radius of the die roll.

4. The cutting device according to claim 1, further comprising:
    a third belt conveyor configured to hold and transport the absorptive article, which is obtained through cutting the continuous portion by the cutting blade, further downstream in the machine direction away from the die roll and the anvil roll,
    wherein the third belt conveyor includes a third upper belt and a third lower belt, which are configured to nip the absorptive article between the third upper belt and the third lower belt.

5. The cutting device according to claim 1, wherein the outer peripheral surface of the first large diameter portion is provided with a nipping member other than the cutting blade and configured to nip the continuous portion of the web between the nipping member and the second large diameter portion.

6. The cutting device according to claim 1, wherein said second belt conveyor and a downstream end of said first belt conveyor are arranged side by side in the cross direction.

7. The cutting device according to claim 6, further comprising:
a third belt conveyor configured to hold and transport the absorptive article, which is obtained through cutting the continuous portion by the cutting blade, further downstream in the machine direction away from the die roll and the anvil roll,
wherein said second belt conveyor and an upstream end of said third belt conveyor are arranged side by side in the cross direction.

8. A cutting device for cutting a web in a process of manufacturing an absorptive article, wherein the web includes, in a cross direction, a first portion and a second portion, said cutting device comprising:
a die roll including a cutting blade configured to cut the first portion of the web; an anvil roll facing the die roll and defining with the cutting blade a region in which the first portion of the web is to be cut;
a first conveyor positioned, in the machine direction, upstream of said region and configured to transport the first portion of the web downstream in the machine direction toward said region; and
a second conveyor configured to transport the second portion of the web downstream in the machine direction along said region;
wherein
said second conveyor and said region are arranged side by side and spaced from each other in the cross direction,
the die roll and the anvil roll include first and second large small diameter portions, respectively, which define together said region;
at least one of the die roll or the anvil roll further includes a small diameter portion coaxial with and smaller in diameter than a corresponding one of the first and second large diameter portions; and
said second conveyor, together with the second portion to be held and transported by said second conveyor, passes through between the die roll and the anvil roll, at a side where the small diameter portion is provided.

9. The cutting device according to claim 8, wherein a distance from an end of the first conveyor adjacent said region to said region is shorter than a radius of at least one of the die roll or the anvil roll.

10. The cutting device according to claim 8, further comprising:
a third conveyor configured to transport the absorptive article, which is obtained through cutting the first portion by the cutting blade, further downstream in the machine direction away from said region,
wherein
the first conveyor includes a first endless belt wound around a first roller upstream of and adjacent to said region;
the third conveyor includes a third endless belt wound around a third roller downstream of and adjacent to said region; and
said first and third conveyors are disconnected from each other and separated, in the machine direction, by said region.

11. The cutting device according to claim 10, wherein said second conveyor extends continuously in the machine direction
from a first position where said second conveyor and said first roller are arranged side by side in the cross direction,
to a second position where said second conveyor and said region are arranged side by side in the cross direction, then
to a third position where said second conveyor and said third roller are arranged side by side in the cross direction.

12. The cutting device according to claim 8, wherein the outer peripheral surface of the die roll has a nipping member other than the cutting blade and configured to nip the first portion of the web between the nipping member and the anvil roll.

13. The cutting device according to claim 8, wherein said second conveyor and a downstream end of said first conveyor are arranged side by side and spaced from each other in the cross direction.

14. The cutting device according to claim 8, further comprising:
a third conveyor configured to transport the absorptive article, which is obtained through cutting the first portion by the cutting blade, further downstream in the machine direction away from said region,
wherein said second conveyor and an upstream end of said third conveyor are arranged side by side and spaced from each other in the cross direction.

* * * * *